United States Patent [19] [11] 4,308,027
Ceriotti [45] Dec. 29, 1981

[54] METHOD AND COMPOSITION FOR DIRECT DETERMINATION OF IRON IN BLOOD SERUM

[75] Inventor: Ferruccio A. R. Ceriotti, Padova, Italy

[73] Assignee: R.C.C. Societa' Ricerche di Chimica Clinica S.r.l., Milan, Italy

[21] Appl. No.: 90,711

[22] Filed: Nov. 2, 1979

[30] Foreign Application Priority Data

Nov. 8, 1978 [IT] Italy .............................. 29543 A/78

[51] Int. Cl.$^3$ ........................................... G01N 33/52
[52] U.S. Cl. ................................. 23/230 B; 252/408; 422/61
[58] Field of Search ..................... 23/230 B; 252/408; 422/61

[56] References Cited

PUBLICATIONS

Ruutu, Det. of Iron & Unsaturated Iron–Binding Capacity in Serum with Ferrozine, Clin. Chim. Acta. 61 (1975), 229–232.
Rice et al., Clin. Chim. Acta. 53 (1974), 391–393.
Yee et al., Clin. Chem., vol. 17, No. 9, 1971.
Duffy et al., Clin. Biochem. 10(3), 122–123 (1977).
Henry et al., Clinical Chem., Prin. & Techniques, 1974, Harper & Row (1974), pp. 679–681.
Stookey, Ferrozine–A New Spectrophotometric Reagent for Iron, Anal. Chem., vol. 42, No. 7, Jun. 1970, 779–781.
Carter et al., Spectrophotometric Det. of Serum Iron at the Submicrogram Level with a New Reagent (Ferrozine), Anal. Biochem. 40, 450–458 (1971).
Persijn et al., Det. of Serum Iron & Latent Iron–Binding Capacity (LIBC), Clin. Chim. Acta. 35 (1971), 91–98.
Improved Direct Specific Det. of Serum Iron & Total Iron-Binding Capacity, Clin. Chem., vol. 26, No. 1980, Ceriotti et al.
White et al., Clin. Chem. 19/51, 526–528 (1973).
Chem. Abstracts 83 (1975), #74953y, Spectrophotometric Determination of Serum Iron Without Deproteinization, Bellina et al.
Narikawa et al., Chem. Abst., vol. 83 (1975), #128398s, Serum Iron Deter. by Fekit.
Feigl; Chem. of Specific Selective & Sensitive Reactions, Acad. Press, 1949, pp. 56–57.

*Primary Examiner*—Michael S. Marcus
*Attorney, Agent, or Firm*—M. R. Johnson

[57] ABSTRACT

A direct method for determination of iron in blood serum comprising reacting the blood serum with ferrozine in the presence of a reducing agent to bring iron ion into divalent form, thiosemicarbazide and hydrochloric acid at a pH between 1.7 and 2.1, without any addition of buffers and tensioactive agents and determining colorimetrically the iron content of the specimen by means of the colored complex formed between iron ion and ferrozine against a reagent blank.

14 Claims, No Drawings

METHOD AND COMPOSITION FOR DIRECT DETERMINATION OF IRON IN BLOOD SERUM

FIELD OF THE INVENTION

This invention relates to a method and the relative compositions to be used for direct determination of iron in blood serum.

BACKGROUND OF THE INVENTION

Several methods are known for direct determination of iron in blood serum. Some of these methods are based on the possibility to form colored complexes between divalent iron ion and complexing agents such as BP (4,7-diphenyl-1,10-phenantroline), TPTZ (2,4,6-tris(2-pyridyl)-s-triazine) and ferrozine [disodium salt of 3-(2-pyridyl)-5,6-bis (4-sulfophenyl)-s-triazine; See L. L. Stookey: Analytical Chemistry, 42, No. 7, 779, 1970] and to determine spectrophotometrically the complex formed. Specific literature states that ferrozine is particularly suitable in that it forms with divalent iron a colored complex of very high absorbancy ($\epsilon = 27.100$) soluble in water and stable at pH between 3.5 and 11 and preferably between 4 and 9.

Most of the methods for determination of iron is serum described in the prior art require (1) dissociation of iron from serum transferrin by treatment with strong mineral acids in the presence of a reducing agent (2) deproteinization of serum through precipitation of proteins, for example, with trichloacetic acid, (3) determination of the bivalent iron ion remaining in the solution through color reaction with ferrozine after the pH of the solution is brought at a value between 3 and 6 with buffer (See P. Carter: Anal. Biochem. 40, 450, 1971).

Other methods are known as "direct" methods, which do not require precipitation of the proteins (See for instance J. P. Persijn et al., Clin. Chim. Acta 35, 91, 1971; J. M. White et al., Clin. Chem. Vol. 19, No. 5, 526, 1973; R. Ruutu: Clin. Chim. Acta 61, 229, 1975).

These methods, generally involve use of buffers in a pH range corresponding to the isoelectric point of most of serum proteins and therefore to their maximum of instability. Precipitation of proteins that would strongly interfere with analytical results is obviated by addition of detergents. These should also operate the detachment of iron from transferrin without lowering the pH. However the variable proteins composition of the various sera does not allow an uniform and stable protection against turbidity formation in every case. In fact, individual differences are not obviated by the reading of the initial absorbance or of the blank in that, in several instances, an unpredictable turbidity may be superimposed to the colored complex. Furthermore the release of iron from transferrin may not be complete giving erroneously low values. For the above reasons the Expert Panel on Iron of the International Committee for Standardization in Haematoglogy has rejected as reference serum iron method all of the numerous "direct" methods without proteins precipitation so far known. (See E. W. Rice et al., Clin. Chim. Acta 53, 391, 1974).

On the other hand, serum deproteinization sensibly lengthens the procedure and constitutes a critical step since serum filtrates, after proteins precipitation, may not be perfectly clear; moreover, a concentrated buffer is required to adjust the pH in a range suitable for the chromogenic reaction and this may be a source of iron contamination. The presence of copper that, under certain pathological circumstance may reach very high levels, can interfere strongly on spectrophotometrical methods, especially those based on the use of ferrozine. (See Hugh et al., Clin. Chem. Vol. 17, No. 9, 950, 1971; J. R. Duffy et al., Clin. Biochem. 10, 122, 1977).

SUMMARY OF THE INVENTION

This invention provides a method and compositions to be used in a form of a diagnostic kit for a determination of iron in serum without requiring deproteinization and separation of iron. The method and the compositions according to this invention have also the advantage that the release of iron from transferrin is complete being obtained at a low pH without addition of buffers, in presence of a reducing agent, under experimental conditions that allow a complete and rapid development of the colored complex, without formation of turbidity, thus avoiding the use of tensioactive agents. The method is very simple and is easily amenable to automation.

The fundamental of this invention is the surprising finding that: (1) by adding hydrochloric acid to serum to reach a pH of 2.1 or lower, no turbidity forms and: (2) the reaction between ferrozine and iron is complete even at these pH, thus allowing very exact measurements of iron content in serum by colorimetric determinations.

Moreover it has been found that the presence of thiosemicarbazide under these conditions eliminates every copper interference without negatively affecting or unsuitably complicating the procedure for iron determination.

According to the direct method of this invention, a serum containing iron to be determined is additioned with hydrochloric acid to bring the pH at a value between 1.6 to 4.0 preferably betwen 1.7 and 2.1. A reducing agent to bring iron ion into divalent form, ferrozine and thiosemicarbazide are also added to the serum sample to be tested. After the addition of these reactants is completed, the sample is carefully mixed and then, after standing at room temperature for 5 to 20 minutes, the iron content of the specimen is determined colorimetrically by means of the colored complex.

Accordingly, absorbance at 562 nm is measured against a reagent blank, i.e. a sample containing the same mixture as above with exclusion of ferrozine. Evaluation of the iron content is made by means of a standard curve obtained from water solutions, buffered at the same pH as the test sample, containing the above reactants and a weighed amount of iron. The hydrochloric acid which is added to serum sample for releasing iron from transferrin to obtain the desired pH is generally in such amount that its concentrations in the test sample is ranging from 0.04 mol/l to 0.15 mol/l, preferably from 0.05 mol/l to 0.12 mol/l. Ascorbic acid is preferably employed as the reducing agent. Concentrations as low as 1.5 mg/ml in the test sample are sufficient to give rise to complete color development. In the usual practice, concentrations from 5 mg/ml to 10 mg/ml are advantageously employed. The color increases by increasing the ferrozine concentration up to 0.4 mg/ml in the test sample. However, complete color development may be observed also at lower concentrations if the reading is made at least 20 minutes after the reaction is made.

For practical purposes, the concentration of ferrozine in the test sample is generally maintained from about 0.4 mg/ml to about 1 mg/ml.

Thiosemicarbazide, even at very low concentrations in the test sample completely prevents copper interference at a pH range between 1.7 and 2.1. At the above pH range thiosemicarbazide is more effective than other agents such as thiourea and does not react with iron. The concentrations of thiosemicarbazide which are usually employed according to an embodiment of this invention are generally ranging between 0.5 mg/ml and 1 mg/ml.

The reaction of the reactants with the serum is generally made by adding to one volume of serum two volumes of a solution containing ascorbic acid, ferrozine and thiosemicarbazide in determined amounts in HCl of appropriate concentration. This latter solution is prepared before carrying out the test and is stable up to two hours.

The reading against the blank can also be performed in the same cuvette wherein the reaction between the reagents and the serum is carried out. In this case, the serum is added first with the solution of the reagents excluding ferrozine and a first reading is taken at 562 nm for the blank.

Then, ferrozine is added in sufficient amount and a second reading is taken at the same wave length for the iron content determination. This possiblity of performing differential readings in a single cuvette reduces both the amount of serum and the number of operations required. In an alternative procedure, the solid reagents can also be added in form of small tablets to the mixture of serum and hydrochloric acid. These tablets may contain the required amount of ascorbic acid and ferrozine or the required amount of thisemicarbazide with common excipients such as carbohydrates derivatives and high molecular weight polyethylene glycols.

The method of this invention gives very satisfactory results when tests to assess reproducibility are carried out on sera at different concentrations.

Moreover, when to samples of pooled sera standard iron solutions are added to increase the sample concentrations, the plot of absorbance values for the added iron concentrations passes through the point of zero addition. Thus, the original iron concentration of the sample can be determined by extrapolating to the abscissa, proving the accuracy of the method. The absorbancy calculated from the addition experiments is coincident with that found with standard iron solutions. The method of this invention was compared with other methods known, both involving deproteinization and direct procedure. Atomic absorption (AA) was chosen (after having ascertained its reliability by reproducibility and recovery experiments) as the method of comparison because it is undoubtedly free from copper interference. Iron was determined on 26 sera covering a large range of concentrations by (1) an automated flow method (AT) (B. Zak et al., Clin. Vol. 11, No. 6, 641, 1965), involving detachment of iron from transferrin, dialysis and complexing with ferrozine; (2) the method of this invention (DRC); the atomic absorption method (AA) involving deproteinization; a commercial direct method identified as DM1 and a commercial direct method identified as DM2.

Both the two latter methods are essentially based on the method described by K. Lauber (Zeit.Klein. Chem. 3, 96, 1965).

The results are reported in the following table I.

TABLE I

| Serum N. | μg of iron per 100 ml of serum | | | | |
|---|---|---|---|---|---|
| | AT | AA | DRC | DR 1 | DR 2 |
| 1 | 4 | 10 | 11 | **70 | **Unreadable |
| 2 | 15 | 17 | 16 | 17 | 20 |
| 3 | 24 | 34 | 36 | *45 | +Unreadable |
| 4 | 33 | 48 | 50 | 45 | 40 |
| 5 | 40 | 40 | 39 | *45 | 35 |
| 6 | 44 | 45 | 44 | 45 | 45 |
| 7 | 51 | 52 | 52 | 39 | 48 |
| 8 | 55 | 55 | 55 | 50 | 40 |
| 9 | 59 | 60 | 58 | 55 | 50 |
| 10 | 66 | 70 | 75 | 55 | 53 |
| 11 | 73 | 72 | 72 | 67 | 60 |
| 12 | 79 | 70 | 66 | 78 | 75 |
| 13 | 82 | 84 | 83 | 72 | 60 |
| 14 | 87 | 88 | 87 | 83 | 70 |
| 15 | 91 | 93 | 97 | 83 | 75 |
| 16 | 94 | 90 | 92 | 89 | 75 |
| 17 | 98 | 96 | 98 | **133 | 100 |
| 18 | 108 | 110 | 108 | 105 | 85 |
| 19 | 120 | 125 | 128 | *128 | 110 |
| 20 | 128 | 127 | 126 | 122 | 112 |
| 21 | 140 | 140 | 138 | **200 | 125 |
| 22 | 150 | 145 | 145 | 134 | 125 |
| 23 | 163 | 155 | 152 | **172 | 140 |
| 24 | 180 | 175 | 180 | 167 | 155 |
| 25 | 213 | 210 | 217 | 194 | 175 |
| 26 | 241 | 238 | 239 | 228 | 225 |

*Formation of turbidity
**Formation of rapidly increasing turbidity
+Slight haemolysis The results of table I show that there is an excellent correlation between the method of this invention and the atomic absorption (AA) method for the entire range of concentrations. For concentrations less than 60 μg/dl and above 160 μg/dl AT is in a less satisfactory correlation with AA that the method of this invention. With the kit DM1 turbidity is frequently observed which in some cases is responsible of erroneously high values. With the kit DM2, in occasional samples, a very rapidly increasing turbidity develops which prevents any possiblity of reading; and even a slight hemolysis has been found to give rise to interferences. Moreover, the values found are usually lower than those obtained with the other methods.

DETAILED DESCRIPTION OF THE METHOD OF THE INVENTION

Solutions (1) 100 mg of thiosemicarbazide, 1 g of ascorbic acid and 100 mg of ferrozine are placed in a 100 ml volumetric flask and then dissolved with 0.1 molar HCl. The solution is brought to volume with 0.1 molar HCl.

(2) The same solution, with exclusion of ferrozine, is prepared for the blank.

The solutions are employed within two hours.

(3) For working standard solutions, 100 mg of thiosemicarbazide, 1 g of ascorbic acid and 100 mg of ferrozine are dissolved with a glicine buffer 0.1 molar at pH 2.1 and brought to 100 ml volumes with the same buffer.

(4) Iron working standards are prepared by appropriate dilutions of a stock standard solution containing 100 μg/ml of 99.9% iron. Solutions at the desired concentrations from 25 to 400 μg/dl are prepared daily.

Procedure

To 2 ml of solution (1) 1 ml of serum is added in a cuvette; the cuvette is covered with a plastic inert film (e.g.: Parafilm ®) and the solution is mixed by inversion. After standing for 5 minutes the solution is mixed again and after additional 5 minutes, the adsorbance at 562 nm is read against a blank prepared by adding 1 ml of serum to 2 ml of solution (2).

For the standard curve, to 2 ml of solution (3) 1 ml of the various iron solutions (4) is added. After mixing, the relative absorbancies are read against the blank by adding to 2 ml of solution (1) to 1 ml of glycine buffer, because traces of iron may be present also in the purest glycine. The absorbancies are plotted against the standard iron concentrations.

When the reaction is carried out in a single curvette, 1 ml of serum is added to 2 ml of solution (2) and a first reading is taken at 562 nm. Then, 100 µl of a 2 g/dl solution of ferrozine are added and, after mixing by repeated inversions and standing for 10 minutes, a second reading at 562 nm is made.

I claim:

1. A direct method for determination of iron in blood serum comprising (a) reacting the blood serum with ferrozine in the presence of a reducing agent to bring iron ion into divalent form, thiosemicarbazide and hydrochloric acid at a pH between 1.7 and 2.1, without any addition of buffers and tensioactive agents and (b) determining colorimetrically the iron content of the specimen by means of the colored complex formed between iron ion and ferrozine against a reagent blank.

2. The method of claim 1 wherein the reducing agent is ascorbic acid.

3. The method of claim 1 wherein the concentration of hydrochloric acid in the test sample submitted to colorimetric measurement is ranging between 0.05 mol/l and 0.12 mol/l.

4. The method of claim 1 wherein the concentration of ferrozine in the test sample submitted to colorimetric determination amounts from 0.4 mg/ml to 1 mg/ml.

5. The method of claim 1 wherein the concentration of thiosemicarbazide in the test sample submitted to colorimetric determination amounts from 0.5 mg/ml to 1 mg/ml.

6. The method of claim 2 wherein the concentration of ascorbic acid in the test sample amounts to at least 1.5 mg/ml.

7. In a method for direct colorimetric determination of iron in blood serum by reacting the serum iron with ferrozine in the presence of acid and a reducing agent to release serum iron from transferrin and reduce iron ion to divalent form the improvement which comprises: carrying out the iron-ferrozine reaction in the presence of sufficient thiosemicarbazide to eliminate significant copper interference, without any addition of buffer and tensioaction agents and at a pH sufficiently low that such elimination of copper interference is obtained without significant reaction of the thiosemicarbazide with iron, said low pH also being such that substantially complete formation of a colored iron-ferrozine complex is obtained.

8. Method of claim 7 wherein the pH is from about 1.7 to about 2.1.

9. A kit for colorimetric determination of iron in blood serum without protein precipitation characterized in that the reagent mixture for colorimetric determination comprises hydrochloric acid, ascorbic acid, ferrozine and thiosemicarbazide and does not require addition of tensioactive agents, the amounts of hydrochloric acid, ferrozine and thiosemicarbazide being such that substantially complete reaction of ferrozine with iron in serum, and substantially complete elimination of copper interference without substantial reaction of iron with thiosemicarbazide is obtained.

10. The kit of claim 9 whereby the reagent mixture is prepared in such a way that in the test sample submitted to colorimetric measurement the concentration of hydrochloric acid ranges between 0.05 mol/l and 0.12 mol/l, the concentration of ascorbic acid ranges between 5 mg/ml and 10 mg/ml, the concentration of ferrozine ranges between 0.4 mg/ml and 1 mg/ml and the concentration of thiosemicarbazide ranges between 0.5 mg/ml and 1/ml.

11. The kit of claim 10 whereby the reagent ferrozine is added as a concentrated solution to the reaction mixture and two photometric readings are made on the sample, one before and the other after the addition of ferrozine.

12. The kit of claim 9 whereby the reactants ferrozine and ascorbic acid and the thiosemicarbazide are added to the mixture of serum and hydrochloric acid in form of tablets.

13. A tablet for use in the kit of claim 12 which contains ferrozine and ascorbic acid together with an inert carrier.

14. A reagent composition for determination of iron in blood serum consisting essentially of ferrozine, thiosemicarbazide, ascorbic acid and sufficient hydrochloric acid to provide a pH of from about 1.7 to about 2.1.

* * * * *